United States Patent
Nomura

[11] Patent Number: 5,834,585
[45] Date of Patent: Nov. 10, 1998

[54] METHOD FOR THE SEPARATION OF HEXAMETHYLCYCLOTRISILOXANE

[75] Inventor: Toshi Nomura, Chiba Prefecture, Japan

[73] Assignee: Dow Corning Toray Silicone Co., Ltd., Tokyo, Japan

[21] Appl. No.: 892,491

[22] Filed: Jul. 14, 1997

[30] Foreign Application Priority Data

Jul. 29, 1996 [JP] Japan .................................. 8-216136

[51] Int. Cl.$^6$ ...................................................... B01D 3/34
[52] U.S. Cl. ........................... 528/501; 556/460; 203/68; 203/69; 203/70
[58] Field of Search ................................ 56/460; 203/68, 203/69, 70; 528/501

[56] References Cited

U.S. PATENT DOCUMENTS 5,660,690  8/1997  Gornowicz et al. ........................ 203/1

*Primary Examiner*—Margaret Glass
*Attorney, Agent, or Firm*—William F. Boley

[57] ABSTRACT

A method for separating hexamethylcyclotrisiloxane that does not require the use of a distillation set up adapted for use with solids and that collects the hexamethylcyclotrisiloxane in the form of an easy-to-handle solution. The method comprising inducing the ascent in the gaseous state of a hexamethylcyclotrisiloxane-containing mixture of polydimethylcyclosiloxanes in a distillation column provided with a sidestream element in the middle region of the column so as to induce the ascent of gaseous hexamethylcyclotrisiloxane to at least the level of the sidestream element, supplying into said distillation column solvent having a boiling point below that of hexamethylcyclotrisiloxane and capable of dissolving hexamethylcyclotrisiloxane, so as to form a liquid mixture of hexamethylcyclotrisiloxane and said solvent in the vicinity of the sidestream element, and withdrawing the said liquid mixture from the sidestream element.

6 Claims, 1 Drawing Sheet

METHOD FOR THE SEPARATION OF HEXAMETHYLCYCLOTRISILOXANE

BACKGROUND OF INVENTION

This invention relates to a method for efficiently separating hexamethylcyclotrisiloxane, which is a solid at ambient temperature, from hexamethylcyclotrisiloxane-containing mixtures of polydimethylcyclosiloxanes without resort to a distillation set up adapted for use with solids.

Hexamethylcyclotrisiloxane is useful as a starting material for the preparation of linear-chain polydimethylsiloxanes and dimethylsiloxane macromonomers. Polydimethylcyclosiloxane makes up about half of the low-degree-of-polymerization polydimethylsiloxane obtained by the hydrolysis of dimethyldichlorosilane. The main components in this polydimethylcyclosiloxane are octamethylcyclotetrasiloxane and lesser amounts of decamethylcyclopentasiloxane, but it contains only traces of hexamethylcyclotrisiloxane. As a result the direct separation of hexamethylcyclotrisiloxane from polydimethylcyclosiloxane mixtures is inefficient. This has led to the proposal of reactions that enrich the hexamethylcyclotrisiloxane content in the polydimethylcyclosiloxane mixture to 5 to 30 mole % (Japanese Patent Application Laid Open (Kokai or Unexamined) Numbers Sho 49-92025 (92,025/1974) and Hei 1-216999 (216,999/1989)).

However, because hexamethylcyclotrisiloxane is a solid compound at ambient temperature (mp=64.5° C.), its separation from a polydimethylcyclosiloxane mixture containing 10 to 30 mole % hexamethylcyclotrisiloxane has required a distillation set up adapted for use with solids. Such a set up requires the use of a device that will maintain a temperature above the melting point of hexamethylcyclotrisiloxane in order to prevent hexamethylcyclotrisiloxane condensation within the condenser at the top of the distillation column, within the conduit running from the condenser to the product receiver, and within the product receiver.

Moreover, since the hexamethylcyclotrisiloxane separated using such a solid-adapted distillation set up is a solid at ambient temperature, its ensuing use for polymerization into linear-chain polydimethylsiloxane or dimethylsiloxane macromonomer requires a preliminary step such as melting or fine comminution.

The object of the present invention is to provide a method for separating hexamethylcyclotrisiloxane that is free of the problems described above. More specifically, the object of the present invention is to provide a method for separating hexamethylcyclotrisiloxane that does not require the use of a solid-adapted distillation set up and that collects the hexamethylcyclotrisiloxane in the form of an easily handled solution.

SUMMARY OF INVENTION

A method for separating hexamethylcyclotrisiloxane that does not require the use of a distillation set up adapted for use with solids and that collects the hexamethylcyclotrisiloxane in the form of an easy-to-handle solution. The method comprising inducing the ascent in the gaseous state of a hexamethylcyclotrisiloxane-containing mixture of polydimethylcyclosiloxanes in a distillation column provided with a sidestream element in the middle region of the column so as to induce the ascent of gaseous hexamethylcyclotrisiloxane to at least the level of the sidestream element, supplying into said distillation column solvent having a boiling point below that of hexamethylcyclotrisiloxane and capable of dissolving hexamethylcyclotrisiloxane, so as to form a liquid mixture of hexamethylcyclotrisiloxane and said solvent in the vicinity of the sidestream element, and withdrawing the said liquid mixture from the sidestream element.

Figure 1:
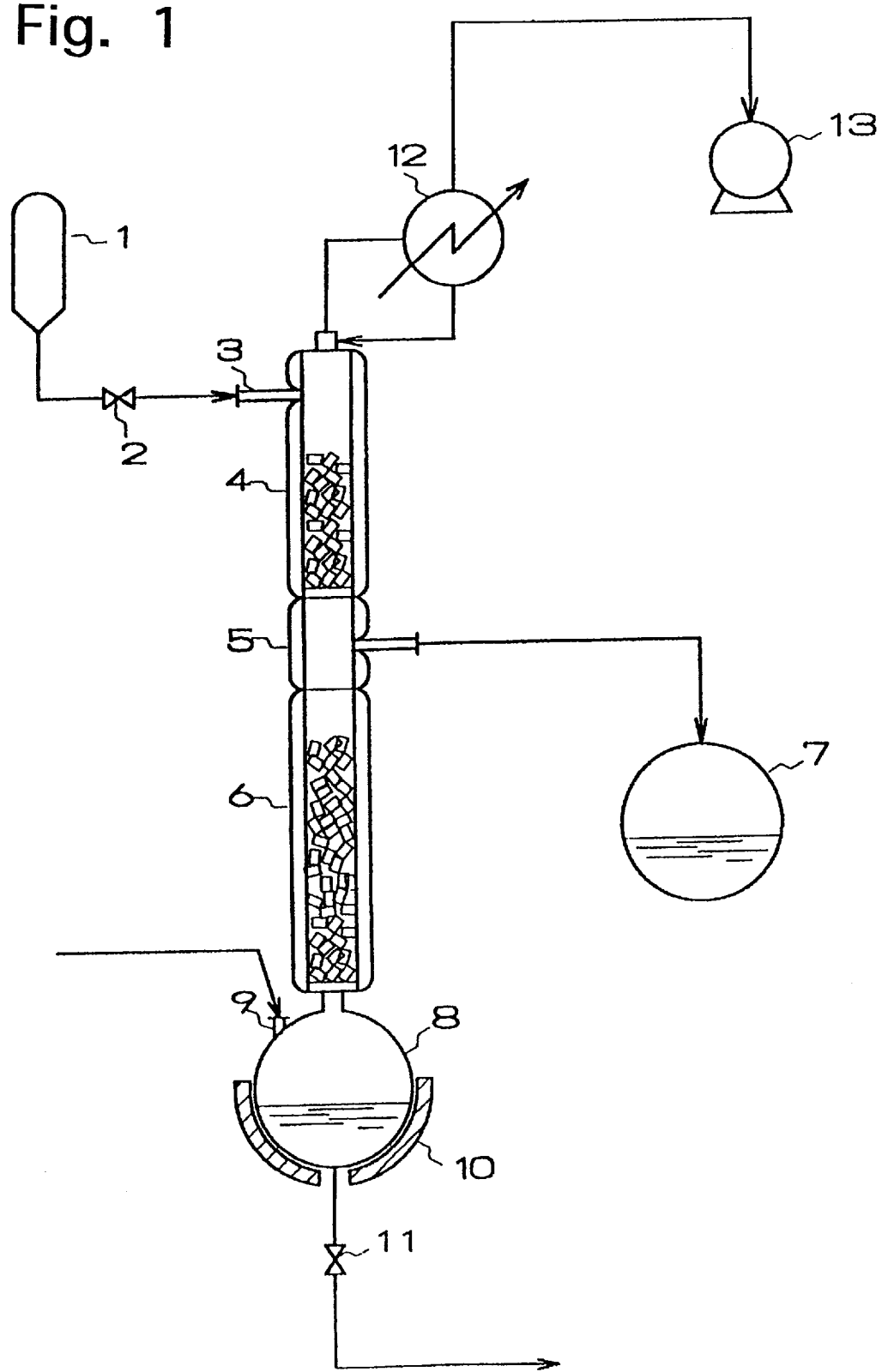
FIG. 1 is a schematic diagram of the distillation set up used in the examples of the invention.

Reference numbers
1 solvent reservoir
2 control valve
3 solvent feed inlet
4 distillation column
5 sidestream element
6 distillation column
7 receiver
8 still
9 starting material feed inlet
10 heater
11 valve
12 condenser
13 vacuum pump

DESCRIPTION OF INVENTION

The present invention is a method for separating hexamethylcyclotrisiloxane from a polydimethylcyclosiloxane mixture as a liquid mixture of hexamethylcyclotrisiloxane and solvent. The method comprises inducing the ascent in the gaseous state of a hexamethylcyclotrisiloxane-containing mixture of polydimethylcyclosiloxanes in a distillation column provided with a sidestream element in the middle region of the column so as to induce the ascent of gaseous hexamethylcyclotrisiloxane to at least the level of the sidestream element, supplying into said distillation column solvent having a boiling point below that of hexamethylcyclotrisiloxane and capable of dissolving hexamethylcyclotrisiloxane, so as to form a liquid mixture of hexamethylcyclotrisiloxane and said solvent in the vicinity of the sidestream element, and withdrawing the liquid mixture from the sidestream element.

The chemical formula for hexamethylcyclotrisiloxane is $((CH_3)_2SiO)_3$. It has a melting point of 64.5° C., a boiling point at atmospheric pressure of 133° C., a specific gravity in the crystalline state of 1.12, and is soluble in many organic solvents. The hydrolysis of dimethyldichlorosilane yields almost equal amounts of polydimethylcyclosiloxanes (cyclics) and silanol-endblocked polydimethylsiloxane (linear chain), with both of these having a low degree of polymerization (DP) and the main components being small oligomers. In industrial applications, the polydimethylcyclosiloxane (main component= octamethylcyclotetrasiloxane) is separated by distilling at elevated temperature and is used as a starting material for polymerization into linear-chain polydimethylsiloxane with higher DPs or as a component in cosmetics.

However, polymerization to give low-dispersity linear-chain polydimethylsiloxane or dimethylsiloxane macromonomer requires the polymerization of hexamethylcyclotrisiloxane using a lithium catalyst. This in turn requires separation of the hexamethylcyclotrisiloxane from the polydimethylcyclosiloxane mixture, which is a mixture of polydimethylcyclosiloxanes with different DPs.

For the purposes of the present separation method, polydimethylcyclosiloxane mixtures useable for hexamethylcyclotrisiloxane separation can be the polydimethylcyclosiloxane mixtures whose hexamethylcyclotrisiloxane content has been enriched to 5 to 30 mole % by contacting a very hexamethylcyclotrisiloxane-poor polydimethylcyclosiloxane mixture with a solid alkali metal catalyst while heating, as disclosed in the above-mentioned Japanese Patent Application Laid Open Numbers Sho 49-92025 and Hei 1-216999. Also useable in the present separation method are the polydimethylcyclosiloxane mixtures disclosed in Japanese Patent Application Laid Open (Kokai) Number Hei 2-129192 (129,192/1990) by contacting linear-chain polydimethylsiloxane with a fixed catalyst bed while heating at reduced pressure in the absence of oxygen, which converts the linear-chain polydimethylsiloxane to cyclics.

In order to separate hexamethylcyclotrisiloxane from the polydimethylcyclosiloxane mixture as a liquid mixture in solvent, the polydimethylcyclosiloxane mixture is introduced, preferably continuously, into the still of a distillation apparatus and the still is heated to evaporate the polydimethylcyclosiloxane mixture and induce its ascent within a distillation column connected to the top of the still. A sidestream element is provided in the middle region of the distillation column. In order to improve the degree of separation of the different DP polydimethylcyclosiloxanes, the column is provided, except at the sidestream element, with plates or a filler, e.g., Helipack or McMahon packing. Since the hexamethylcyclotrisiloxane in the polydimethylcyclosiloxane mixture has a lower boiling point than the other different DP members of the mixture, it will reach to at least the level of the sidestream element while being at the highest position of the polydimethylcyclosiloxanes within the column. For the purposes of the present invention, "at least the level of the sidestream element" denotes the level of the sidestream element itself or a higher position. Octamethylcyclotetrasiloxane (DP=4) has a boiling point (atmospheric pressure) of 171° C.; decamethylcyclopentasiloxane (DP=5) has a boiling point (atmospheric pressure) of 204.5° C.; and dodecamethylcyclohexasiloxane (DP=6) has a boiling point (atmospheric pressure) of 236° C.

The distillation column is at the same time fed with a solvent that has a boiling point below that of hexamethylcyclotrisiloxane and that is capable of dissolving hexamethylcyclotrisiloxane. The solvent feed position is not critical, and the solvent may be fed to the column top or at a position above or below the column middle. When the solvent is fed from the column top, it descends within the distillation column and produces a liquid mixture upon contacting the evaporated hexamethylcyclotrisiloxane that has reached at least the level of the sidestream element.

When the solvent is introduced beneath the column middle, it is evaporated by heat input from the gaseous polydimethylcyclosiloxane mixture and reaches at least the level of the sidestream element. The drop in temperature causes the solvent to liquefy and the solvent then produces a liquid mixture upon contacting the evaporated hexamethylcyclotrisiloxane that has reached at least the level of the sidestream element.

The pressure within the still and distillation column is not critical, but pressures of 100 to 500 torr are preferred from the standpoint of operating efficiency.

No particular restrictions apply to the hexamethylcyclotrisiloxane-dissolving solvent except that it should have a boiling point below that of hexamethylcyclotrisiloxane and should form a stable solution of hexamethylcyclotrisiloxane. In addition to toluene, the subject solvent is exemplified by benzene, n-hexane, n-heptane, n-octane, cyclohexane, isopropyl alcohol, ethyl propyl ether, diisopropyl ether, dipropyl ether, ethyl isopentyl ether, ethyl acetate, propyl acetate, butyl acetate, carbon tetrachloride, and tetrahydrofuran.

The top of the distillation column is preferably connected to a condenser. As a result of this, gaseous hexamethylcyclotrisiloxane and gaseous solvent reaching the region above the column top will be cooled and liquefied in the condenser and will then descend into the distillation column.

The sidestream element is provided in the middle region of the distillation column, and a side conduit exits from the sidestream element to the outside to a receiver. The hexamethylcyclotrisiloxane plus solvent liquid mixture generated in the vicinity of the sidestream element flows from the sidestream element through the side conduit and into the receiver. This yields a solution of pure hexamethylcyclotrisiloxane, from which the solvent can be distilled as desired to produce pure hexamethylcyclotrisiloxane.

The sidestream element need merely be in the middle region of the column and is not limited to precisely the halfway point along the distillation column.

The sidestream element preferably also performs a reflux function in which part of the liquid mixture is discharged from the system and the remainder is returned to the distillation column below the sidestream element and ultimately to the still. The separation efficiency between hexamethylcyclotrisiloxane and octamethylcyclotetrasiloxane can be improved by this discharge of part of the liquid mixture from the system and return of the remainder to the distillation column below the sidestream element and ultimately to the still. The ratio of the liquid mixture taken from the system to the liquid mixture returned to the lower distillation column (below, the reflux ratio) is not critical.

The following are preferably carried out continuously from the standpoint of operating efficiency: the feed of the polydimethylcyclosiloxane mixture to the still, the feed to the distillation column of solvent that has a boiling point below that of hexamethylcyclotrisiloxane and can dissolve hexamethylcyclotrisiloxane, and the withdrawal of the liquid mixture of hexamethylcyclotrisiloxane and solvent.

EXAMPLES

The invention will be explained below through working examples, in which "%" indicates "weight percent".

Example 1

In this example, the upper and lower columns were, respectively, glass distillation column 4 with a height of 300 mm and glass distillation column 6 with a height of 500 mm, each of which were vacuum-jacketed and had an internal diameter of 15 mm. Glass sidestream element 5 was connected between these two columns. This element was vacuum-jacketed, had a height of 250 mm, and had a reflux capability. Condenser 12 was connected to the top of 300-mm distillation column 4 and 500-mL glass still 8 was connected to the bottom of 500-mm distillation column 6. Helipack #2 (1.25 mm×2.5 mm×2.5 mm) packing was used: it was packed to a height of 150 mm in 300-mm distillation column 4 and to a height of 400 mm in 500-mm distillation column 6. The starting material was a polydimethylcyclosiloxane mixture that contained 7.0% hexamethylcyclotrisiloxane, 64.9% octamethylcyclotetrasiloxane, 24.7% decamethylcyclopentasiloxane, and a total of 4.5% polydimethylcyclosiloxane with DP≧6. This starting material was fed to still 8 through starting material feed inlet 9. Still 8 was heated to about 156° C. using heater 10 and a gaseous polydimethylcyclosiloxane mixture was driven up distillation column 6. Toluene was fed as solvent from solvent reservoir 1 through solvent feed inlet 3 provided in the upper zone of 300-mm distillation column 4. The solvent descended in distillation column 4 and came into contact with gaseous hexamethylcyclotrisiloxane that had reached to at least side stream element 5. 20 g/hour of a mixed liquid of 37% hexamethylcyclotrisiloxane and 63% toluene was collected in receiver 7 when the distillation was run continuously using the following conditions: 1:6 for the reflux ratio at the sidestream element, 10 g/hour for the feed rate of hexamethylcyclotrisiloxane in the starting material, 15 g/hour for the toluene feed rate, and 500 torr for the pressure within still 8. During this process the temperature of the mixed liquid at sidestream element 5 was 84° C.

Example 2

A continuous distillation was run using the same conditions as in Example 1, but in this case using benzene as the solvent instead of toluene. 19 g/hour of a mixed liquid of 38% hexamethylcyclotrisiloxane and 62% benzene was collected in receiver 7. During this process the temperature of the mixed liquid at sidestream element 5 was 60° C.

I claim:

1. A method for separating hexamethylcyclotrisiloxane from a polydimethylcyclosiloxane mixture as a liquid mixture of hexamethylcyclotrisiloxane and solvent comprising inducing the ascent in the gaseous state of a hexamethylcyclotrisiloxane-containing mixture of polydimethylcyclosiloxanes in a distillation column provided with a sidestream element in the middle region of the column so as to induce the ascent of gaseous hexamethylcyclotrisiloxane to at least the level of the sidestream element, supplying into the distillation column a solvent having a boiling point below that of hexamethylcyclotrisiloxane and capable of dissolving hexamethylcyclotrisiloxane, so as to form a liquid mixture of hexamethylcyclotrisiloxane and the solvent in the vicinity of the sidestream element, and withdrawing the liquid mixture from the sidestream element.

2. The separation method according to claim 1, where the solvent is supplied to the top of the distillation column and descends within the column to form the liquid mixture with hexamethylcyclotrisiloxane in the vicinity of the sidestream element.

3. The separation method according to claim 1, where the supply of the solvent and polydimethylcyclosiloxane mixture and withdrawal of the liquid mixture are carried out continuously.

4. The separation method according to claim 1, where the solvent is toluene.

5. The separation method according to claim 1, where the solvent is benzene.

6. The separation method according to claim 1, where the solvent is toluene and the toluene is fed to the top of the column and the supply of toluene and polydimethylcyclosiloxane mixture and withdraw of the liquid mixture are carried out continuously.

* * * * *